Figure 1:
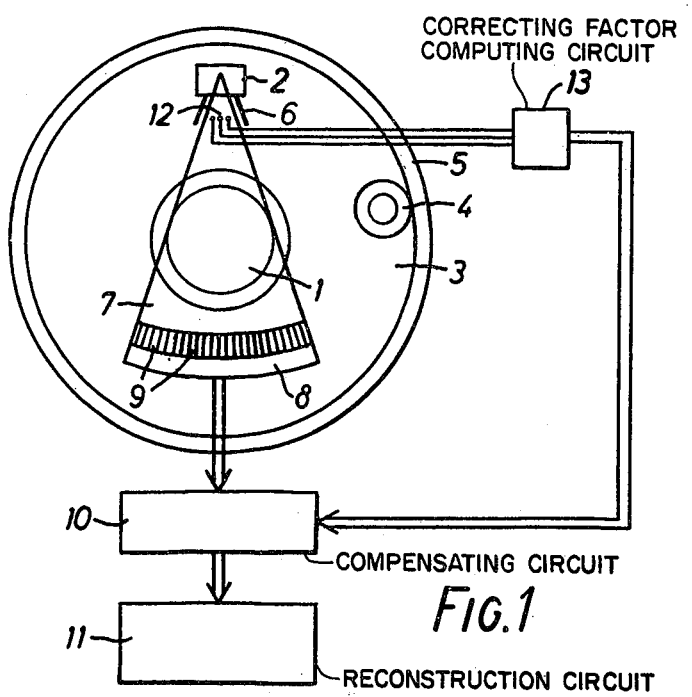

United States Patent [19]

Hounsfield

[11] 4,069,422

[45] Jan. 17, 1978

[54] APPARATUS FOR EXAMINING OBJECTS BY MEANS OF PENETRATING RADIATION

[75] Inventor: Godfrey Newbold Hounsfield, Newark, England

[73] Assignee: E M I Limited, Hayes, England

[21] Appl. No.: 659,155

[22] Filed: Feb. 18, 1976

Related U.S. Application Data

[62] Division of Ser. No. 474,767, May 30, 1974, Pat. No. 3,940,625.

[51] Int. Cl.² ............................................. G01N 23/06
[52] U.S. Cl. ................................ 250/445 T; 250/360; 250/510
[58] Field of Search ..................... 250/360, 445 T, 510

[56] References Cited

U.S. PATENT DOCUMENTS

| 3,134,903 | 5/1964 | Fengler | 250/510 |
|---|---|---|---|
| 3,432,657 | 3/1969 | Slavin | 250/369 X |
| 3,737,660 | 6/1973 | Ando et al. | 250/445 T X |
| 3,755,672 | 8/1973 | Edholm et al. | 250/510 X |
| 3,778,614 | 12/1973 | Hounsfield | 250/360 X |

*Primary Examiner*—Archie R. Borchelt
*Attorney, Agent, or Firm*—Fleit & Jacobson

[57] ABSTRACT

In an apparatus for examining a body by means of penetrating radiation, a source directs a fan-shaped distribution of radiation through a slice of a patient. Detectors disposed on the other side of the body provide measurements of the intensity of the radiation for processing to derive a representation of absorption in the slice. Variations of the hardness of the radiation, with angular position in the fan-shaped distribution, can cause errors in the representation. Means are provided for compensating such variations of hardness; the means being in one example a wedge-shaped compensator inserted into the path of the radiation.

5 Claims, 5 Drawing Figures

APPARATUS FOR EXAMINING OBJECTS BY MEANS OF PENETRATING RADIATION

This is a division of application Ser. No. 474,767, filed May 30, 1974, now U.S. Pat. No. 3,940,625.

This invention relates to apparatus for examining objects by means of penetrating radiation, such as X-radiation.

In our British patent specification No. 1,283,915 there is described apparatus for examining a plane section or slice of a body by penetrating radiation in such a way that an image of the absorption or transmission of the small elements of the slice can be reconstructed. In some examples of apparatus such as described in the said Patent Specification, it is required that the X- radiation be provided in the form of a sectoral swath of radiation. In this case, a group of detectors are provided to detect radiation travelling in narrow paths from the source to the detectors. The source and the detectors are moreover rotatable about an axis normal to the plane of the swath so that a series of outputs can be obtained from each detector for a series of different angular positions of the respective beams. Each detector thus provides an indication of the transmission of the body to the radiation along a number of beams. The image reconstruction is then carried out utilising the series of output signals.

When the X-radiation is provided in the form of a sectoral swath, it is desirable to have a high radiation output from the source of radiation so that an adequate input can be measured by each detector in a relatively short time interval, to produce one of said output signals. To achieve the desired high radiation output, a rotating anode Coolidge tube can be employed. In such a tube the rotating anode has a slant edge from which X-radiation is produced by an electron stream from the cathode. The necessary swath of radiation can be produced by collimating the X-radiation and there are a number of directions in which the radiation can be collimated, although there is also a number of directions which are unsuitable for collimation because of the proximity of the cathode. Difficulties arise however because the probabilty distribution of X-radiation over a swath produced by collimation is not in general uniform, and may also vary with rotation of the anode, whereas accurate image reconstruction requires that the radiation density of each beam should be known.

The object of the present invention is to reduce this difficulty.

According to the invention there is provided apparatus for examining objects by means of penetrating radiation including means for generating radiation emitted in many directions, means for collimating said radiation to produce a substantially planar swath of said radiation, and detecting means for monitoring the intensity of the radiation at spaced positions across the width of the swath, means for deriving output signals representative of the transmission of said radiation along a plurality of laterally spaced beam paths extending longitudinally of the swath, and means for modifying said output signals in response to signals derived from said detecting means.

Preferably moreover said means for generating radiation includes a rotating anode tube in which the anode has a bevelled circumferential margin from which radiation is emitted on operation of the tube, and in which the said collimating means is arranged to produce a swath of radiation which is, or of which the mean axis is, tangential or nearly tangential of said surface.

Figure 2:
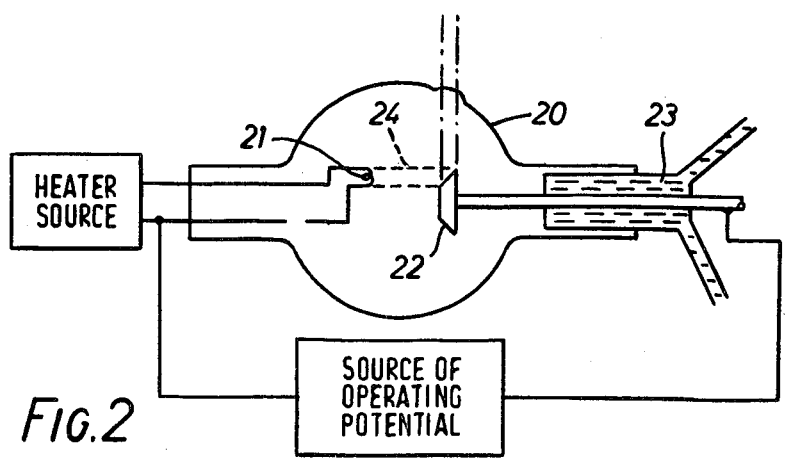
Figure 3:
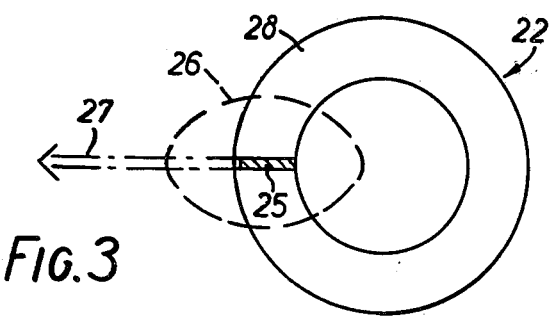
Figure 4:
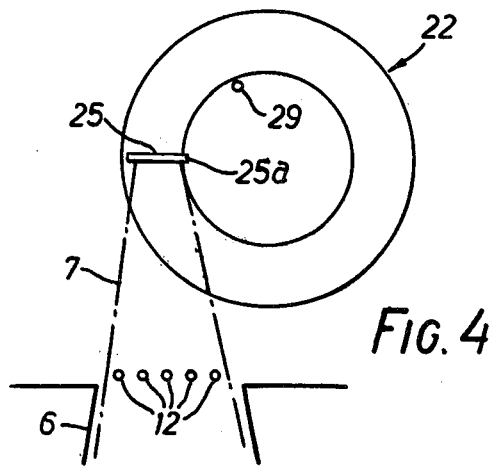
Figure 5:
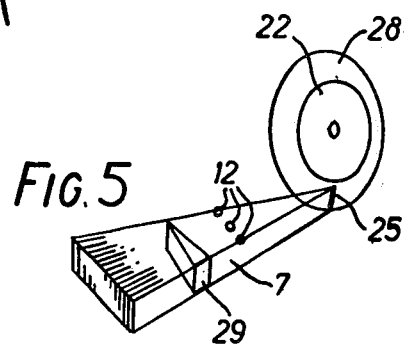

In order that the invention may be clearly understood and readily carried into effect, the same will now be more fully described, by way of example only, with reference to the accompanying drawings, of which:

FIG. 1 is a diagrammatic representation of an apparatus for examining an object by means of penetrating radiation embodying the present invention, FIG. 2 shows schematically, in cross-sectional view, a form of a rotating anode Coolidge tube, which may be used in apparatus such as illustrated in FIG. 1, as a source of X-radiation, FIG. 3 shows, on an enlarged scale, a front elevational view of the rotating anode and, superimposed thereon, a probability distribution function for X-radiation, FIG. 4 shows, in similar view to FIG. 2, the direction in which X-radiation, emitted by the rotating anode, is collimated in accordance with an example of this invention, and FIG. 5 shows another and preferred direction in which radiation is collimated in accordance with another example of the invention.

Referring to FIG. 1, the apparatus therein diagrammatically illustrated is intended for examining planar sections of the human body by means of X-rays in such a way that an image can be reconstructed of the absorption or transmission of the elementary areas of the section, with respect to the X-radiation. The apparatus comprises a patient locating member 1 having an aperture in which the part of the body to be examined can be inserted. The member 1 is fixed in relation to the frame of the apparatus, which is not shown. A chair or table for the patient is provided in fixed relationship to the frame. An X-ray source 2 is fixed to a scanning annulus 3 which is adapted to rotate round the member 1, an electric motor 4 which drives on a peripheral ring 5 of the annulus 3, being provided for rotating the annulus at a constant rate during the examination of the patient. The X-ray source 2 is provided with a collimator 6 which collimates the radiation from the source 2 into a thin planar sectoral swath 7 the angular subtense of which is sufficient to enclose the aperture in the member 1. The swath is thin in the dimension normal to the plane of the drawing so that only a thin section or slice of the patient is traversed by the swath of X-rays. A bank of detectors 8, each with an individual collimator 9, is arranged to receive radiation after traversing the aperture in the member 1, the collimators 9 being such that each detector receives radiation substantially only from a narrow beam extending longitudinally of the swath. The respective detectors therefore derive output signals representative of the transmission of the radiation along a plurality of laterally spaced beam paths. As the annulus 3 rotates successive output signals are derived from the various detectors 8, so that there are derived many groups of signals from the detectors 8, corresponding to different angular positions of the annulus 3. These signals are passed via a compensating circuit 10 to an image reconstruction circuit 11 in which an image is produced representing the variable transmission or absorption of the slice under examination. The operation of the reconstruction circuit 11 need not be described since it may be of any suitable form, such for example that described in the aforesaid British patent specification No. 1,283,915. This describes an iterative reconstruction method, but a method involving convolution or other logical process may equally be used.

The accuracy of reconstruction depends in substantial degree on the accuracy of the measurement of the absorption suffered by any particular beam impinging a detector 8. This requires an accurate knowledge of the intensity of each beam at the point where it emerges from the source 2. With a large area swath of radiation such as 7, which as will appear may be derived from a rotating anode Coolidge tube, the density distribution may vary substantially within the swath. To reduce this disadvantage a plurality of detectors 12 (three are illustrated in the figure) are located just at the aperture of the collimator 6, and so as to intercept radiation adjacent one major surface of the swath 7. The detectors 12 monitor the intensity of the radiation at spaced positioning across the width of the swath.

Corresponding monitoring signals are derived from the detectors 12, and applied to a computing circuit 13 which derives a correcting factor for each beam of the swath, as determined by the collimators 9. Three detectors 12 are illustrated on the assumption that the law of distribution of intensity of radiation across the swath follows a substantially parabolic law, in which case three detectors are sufficient to determine the law. However the number of detectors may be varied according to the accuracy required. The correcting factors derived in the circuit 13 are applied to the compensating circuit 10 to correct the output signals from the various detectors 9 in required manner. The circuit 10 though shown separately from the image reconstruction circuit 11 may be included therein in any convenient position.

The source of radiation 1 is a rotating anode Coolidge tube, such tube being used so that the intensity of radiation in each beam may be sufficiently high for accurate image reconstruction. As shown in FIG. 2 a rotating anode tube comprises in essence a highly evacuated enclosure bounded by an envelope 20, constructed for example of Pyrex glass, a cathode 21, and a rotatable anode 22 mounted within said enclosure. A water jacket 23 provides a heat sink for the anode 22. The anode 22 has a bevelled circumferential margin 28 as shown to present an angled target surface to an electron beam 24 which, in accordance with a feature of the invention, is incident thereon in the manner of a radially disposed slit 25 (see FIG. 2). In response to the bombardment of said target surface by the electron beam 24, X-radiation is emitted in substantially all directions from said target surface in accordance with a probability distribution function the nature of which can be gathered from the dashed outline 26 in FIG. 3. This indicates the function for a plane tangent to the margin 28 at the slit 25. It has been conventional hitherto to surround the tube 1 with a lead enclosure (not shown) which is formed with a window having a collimator attached thereto, the window being sited so as to receive X-radiation emitted along a beam in the direction shown at 27 in FIG. 3 — i.e. the direction in which the probability distribution function 26 assumes a maximum value. It will be observed, however, that the value of the function 27 falls off rapidly on either side of the maximum value, so that it is necessary to limit the size of said window to accommodate only a thin pencil beam in order that the probability distribution function be maintained substantially constant over the cross-sectional dimensions of the pencil beam.

In accordance with an important feature of the invention, however, the window and the collimator 6 are sited so as to accept X-radiation which is substantially rectangular in cross-section and substantially sectoral shaped in plan, so as to form the swath 7. The centre line of swath 7 is substantially orthogonal to the centre line of the electron beam 24. In other words, the swath 7 extends substantially tangentially of the target surface 28 of the anode 22 whereas the electron beam 24 extends substantially radially thereof. Because, across the width of swath 7, the probability distribution function 26 exhibits a broad minimum value, only a limited variation in probability occurs across the width of the swath despite its extended size compared with the corresponding dimension of the electron beam 24.

The variation of function 26 across the width of swath 7 is monitored as aforesaid by means of the plurality of radiation detectors 12, dispersed in an array across said width within the aforementioned lead enclosure and in a plane slightly offset from upper or lower plane of the window in said enclosure so that the detectors 12 do not affect the passage of radiation through said window. The detectors 12 therefore intercept radiation adjacent to the upper or lower major surfaces of the swath. Variation in emission of radiation across the width of swath 7 can thus be compensated for.

Since the anode 22 rotates, it is possible that different parts thereof may exhibit different emission characteristics and thus it can be advantageous to obtain a detailed correlation of emission characteristics with rotation of the anode 22. This can be done utilising information derived from the detectors 12 and from the drive circuit (not shown) used for rotating the anode 22. In order to establish a datum point for each revolution of the anode, however, and in accordance with a refinement of this invention, the incidence of the electron beam on the target surface of anode 22 is adjusted to that of the slit 25 (FIG. 3) is extended inwards of the inner diameter of said target surface, as shown at 25a in FIG. 4. A spot 29 of fluorescent material is provided just inside the inner periphery of the target surface so that the part 25a of the electron beam will strike it once per revolution of anode 22, thus causing it to fluoresce and provide a light output signal which can be detected by a suitable photo detector (not shown).

The preferred construction of the collimator is however illustrated in FIG. 5. In this case, the collimator, which is not illustrated since its construction will be clear, is arranged to select a swath of radiation 6 which is substantially perpendicular to the slit 25, i.e. the narrow strip on the anode on which the electron beam 24 impinges. With this arrangement the slit on strip 25 determines the depth of the slice to be examined. This arrangement has the advantage of providing a more uniform density distribution of radiation in the depth dimension of the swath as well as improving the uniformity of distribution across the width of the swath.

When the X-radiation is derived from the anode over a substantial angular spread in a plane normal to the emitting surface, as in the case of the swath 7 in FIG. 5, the beam tends to vary in hardness in accordance with the angle at which the rays emerge from the surface of the anode. In the example of FIG. 5, this is compensated for by an absorbing wedge 29 which absorbs selectively according to angle. The wedge is shaped with the object of ensuring that hardness of the X-radiation is substantially independent of angle so that it will have substantially uniform absorption properties with respect to the body which is examined.

Other embodiments of the invention will be evident to those skilled in the art and the preceding embodiment has been described by way of example only.

What I claim is:

1. A medical radiographic apparatus including,
   a. a source, arranged to irradiate a slice of an object with radiation projected in different directions in a substantially planar fan-shaped distribution about a mean direction,
   b. detector means, sensitive to the radiation and disposed to receive and to provide output signals indicative of the intensity of radiation emergent from the object in the plane of the distribution,
   c. means for moving the source and the detector means, in the plane of the distribution, relative to the object, to irradiate the object from a plurality of different mean directions,
   d. means for processing the output signals provided by the detector to derive a representation of the variation of absorption of the radiation in said slice of the object and,
   e. means adapted to compensate for variations in the hardness of radiation projected in different directions in the plane of the distribution.

2. An apparatus according to claim 1 wherein said means adapted to compensate is a further object, disposed in the path of the radiation, having different absorptions for radiation emitted at different directions in the plane of the distribution.

3. An apparatus according to claim 2 wherein said further object has an absorbing path length, to the radiation, which is continuously variable with angular position, relative to the source, in the plane of the distribution.

4. An apparatus according to claim 3 wherein said further object is wedge-shaped.

5. An apparatus according to claim 2 wherein said further object is disposed between the source and the first mentioned object.

* * * * *

UNITED STATES PATENT OFFICE
CERTIFICATE OF CORRECTION

PATENT NO. : 4,069,422
DATED : January 17, 1978
INVENTOR(S) : GODFREY NEWBOLD HOUNSFIELD It is certified that error appears in the above-identified patent and that said Letters Patent are hereby corrected as shown below:

On the title page, insert

-- [30] Foreign Application Priority Data

June 1, 1973   United Kingdom ..............26325/73 --

*Signed and Sealed this*

*Thirty-first* Day of *October 1978*

[SEAL]

Attest:

RUTH C. MASON
*Attesting Officer*

DONALD W. BANNER
*Commissioner of Patents and Trademarks*